United States Patent
Grauert et al.

(10) Patent No.: US 7,429,601 B2
(45) Date of Patent: *Sep. 30, 2008

(54) ESTERS OF HYDROXYL-SUBSTITUTED NITROGEN HETEROCYCLES, PROCESSES FOR THE PREPARATION THEREOF AS WELL AS THE USE THEREOF AS PHARMACEUTICAL COMPOSITIONS

(75) Inventors: Matthias Grauert, Biberach (DE); Michael P. Pieper, Biberach (DE); Gerald Pohl, Biberach (DE); Georg Speck, Ingelheim am Rhein (DE); Steffen Breitfelder, Assmannshardt (DE)

(73) Assignee: Boehringer Ingelheim Pharma GmbH & Co. Kg,, Ingelheim (DE)

( * ) Notice: Subject to any disclaimer, the term of this patent is extended or adjusted under 35 U.S.C. 154(b) by 238 days.

This patent is subject to a terminal disclaimer.

(21) Appl. No.: 11/270,303

(22) Filed: Nov. 9, 2005

(65) Prior Publication Data
US 2006/0058344 A1    Mar. 16, 2006

Related U.S. Application Data

(63) Continuation of application No. 10/396,147, filed on Mar. 25, 2003, now Pat. No. 7,094,788.

(60) Provisional application No. 60/386,162, filed on Jun. 5, 2002.

(30) Foreign Application Priority Data
Apr. 13, 2002   (DE) .................. 102 16 339

(51) Int. Cl.
| | | |
|---|---|---|
| A01N 43/42 | (2006.01) |
| A61K 31/34 | (2006.01) |
| C07D 401/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| C07D 421/00 | (2006.01) |

(52) U.S. Cl. ................ 514/304; 546/125; 546/126; 546/127

(58) Field of Classification Search ................ 546/125, 546/126, 127; 514/304
See application file for complete search history.

(56) References Cited

U.S. PATENT DOCUMENTS

| 4,042,700 | A | 8/1977 | Banholzer et al. |
| 5,610,163 | A | 3/1997 | Banholzer et al. |
| 5,654,314 | A | 8/1997 | Banholzer et al. |
| 6,706,726 | B2 | 3/2004 | Meissner et al. |
| 7,094,788 | B2 * | 8/2006 | Grauert et al. ............ 514/304 |
| 2003/0229227 | A1 | 12/2003 | Morschhaeuser et al. |
| 2004/0087617 | A1 | 5/2004 | Meissner et al. |
| 2005/0038252 | A1 | 2/2005 | Morschhaeuser et al. |
| 2005/0197357 | A1 | 9/2005 | Meissner et al. |

FOREIGN PATENT DOCUMENTS

| WO | WO 92/16528 A | 10/1992 |
| WO | WO02/04402 A | 1/2002 |

OTHER PUBLICATIONS

Ionkova et al., "Spectrum of tropane alkaloids in transformed roots of Datura innoxia and Hyoscyamus x gyorffyi cultivated in vitro", Planta Medica, 1994, vol. 60, pp. 382-384.*

Van Zwieten, et al. Cardiovascular drugs and therapy / sponsored by the International Society of Cardiovascular Pharmacotherapy, 1995, 9 (1): 159-167.

Xu, et al. Chemical & Pharmaceutical Bulletin, 1998, 46 (2): 231-241.

* cited by examiner

*Primary Examiner*—D. Margaret Seaman
*Assistant Examiner*—Niloofar Rahmani
(74) *Attorney, Agent, or Firm*—Michael P. Morris; Mary-Ellen M. Devlin; Wendy A. Petka

(57) ABSTRACT

The present invention relates to new compounds of general formula 1

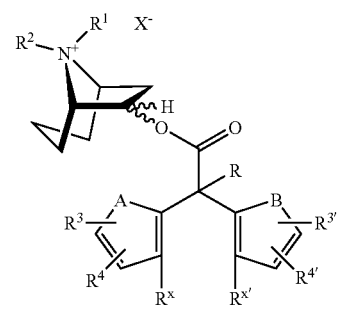

wherein $X^-$ and the groups A, B, R, $R^1$, $R^2$, $R^3$, $R^{3'}$, $R^4$, $R^{4'}$, $R^x$ and $R^{x'}$ may have the meanings given in the claims and in the specification, processes for preparing them and their use as pharmaceutical compositions.

10 Claims, No Drawings

ESTERS OF HYDROXYL-SUBSTITUTED NITROGEN HETEROCYCLES, PROCESSES FOR THE PREPARATION THEREOF AS WELL AS THE USE THEREOF AS PHARMACEUTICAL COMPOSITIONS

This application is a continuation of Ser. 10/396,147, filed Mar. 25, 2003, now U.S. Pat. No. 7,094,788, this application claims the benefit of U.S. Provisional Application Ser. No. 60/386,162, filed on Jun. 5, 2002, both of the above applications are hereby incorporated by reference.

FIELD OF THE INVENTION

The present invention relates to new compounds of general formula 1

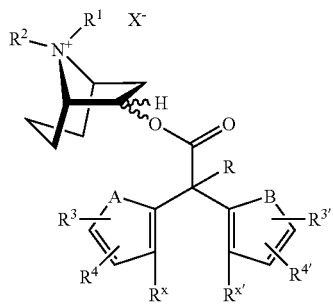

wherein $X^-$ and the groups A, B, R, $R^1$, $R^2$, $R^3$, $R^{3'}$, $R^4$, $R^{4'}$, $R^x$ and $R^{x'}$ may have the meanings given in the claims and in the specification, processes for preparing them and the use thereof as pharmaceutical compositions.

DESCRIPTION OF THE INVENTION

The present invention relates to compounds of general formula 1

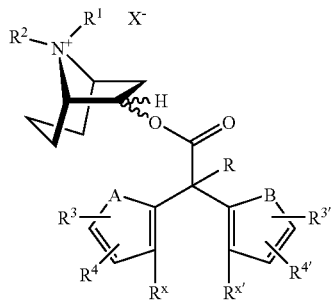

wherein
- $X^-$ denotes an anion with a single negative charge, preferably an anion selected from the group consisting of chloride, bromide, iodide, sulphate, phosphate, methanesulphonate, nitrate, maleate, acetate, citrate, fumarate, tartrate, oxalate, succinate, benzoate and p-toluenesulphonate;
- A and B which may be identical or different, preferably identical, denote —O—, —S—, —NH—, —CH$_2$—, —CH=CH—, or —N($C_1$-$C_4$-alkyl)-;
- R denotes hydrogen, hydroxy, —$C_1$-$C_4$-alkyl, —$C_1$-$C_4$-alkyloxy, —$C_1$-$C_4$-alkylene-halogen, —O—$C_1$-$C_4$-alkylene-halogen, —$C_1$-$C_4$-alkylene-OH, —CF$_3$, CHF$_2$, —$C_1$-$C_4$-alkylene-$C_1$-$C_4$-alkyloxy, —O—COC$_1$-$C_4$-alkyl, —O—COC$_1$-$C_4$-alkylene-halogen, —$C_1$-$C_4$-alkylene-$C_3$-$C_6$-cycloalkyl, —O—COCF$_3$ or halogen;
- $R^1$ and $R^2$ which may be identical or different denote —$C_1$-$C_5$-alkyl, which may optionally be substituted by —$C_3$-$C_6$-cycloalkyl, hydroxy or halogen, or
- $R^1$ and $R^2$ together denote a —$C_3$-$C_5$-alkylene-bridge;
- $R^3$, $R^4$, $R^{3'}$ and $R^{4'}$, which may be identical or different denote hydrogen, $C_1$-$C_4$-alkyl, $C_1$-$C_4$-alkyloxy, hydroxy, —CF$_3$, —CHF$_2$, CN, NO$_2$ or halogen;
- $R^x$ and $R^{x'}$ which may be identical or different denote hydrogen, $C_1$-$C_4$-alkyl, $C_1$-$C_4$-alkyloxy, hydroxy, —CF$_3$, —CHF$_2$, CN, NO$_2$ or halogen or
  - $R^x$ and $R^{x'}$ together denote a single bond or a bridging group selected from the bridges —O, —S, —NH, —CH$_2$, —CH$_2$—CH$_2$—, —N($C_1$-$C_4$-alkyl), —CH($C_1$-$C_4$-alkyl)- and —C($C_1$-$C_4$-alkyl)$_2$.

Compounds of general formula 1 are preferred wherein
- $X^-$ denotes an anion with a single negative charge selected from among the chloride, bromide, 4-toluenesulphonate and methanesulphonate, preferably bromide;
- A and B which may be identical or different, preferably identical, denote —O, —S, —NH or —CH=CH—;
- R denotes hydrogen, hydroxy, —$C_1$-$C_4$-alkyl, —$C_1$-$C_4$-alkyloxy, —CF$_3$, —CHF$_2$, fluorine, chlorine or bromine;
- $R^1$ and $R^2$ which may be identical or different, denote $C_1$-$C_4$-alkyl, which may optionally be substituted by hydroxy, fluorine, chlorine or bromine, or
- $R^1$ and $R^2$ together denote a —$C_3$-$C_4$-alkylene-bridge;
- $R^3$, $R^4$, $R^{3'}$ and $R^{4'}$, which may be identical or different, denote hydrogen, $C_1$-$C_4$-alkyl, $C_1$-$C_4$-alkyloxy, hydroxy, —CF$_3$, —CHF$_2$, CN, NO$_2$, fluorine, chlorine or bromine;
- $R^x$ and $R^{x'}$ which may be identical or different denote hydrogen, $C_1$-$C_4$-alkyl, $C_1$-$C_4$-alkyloxy, hydroxy, —CF$_3$, —CHF$_2$, CN, NO$_2$, fluorine, chlorine or bromine or
  - $R^x$ and $R^{x'}$ together denote a single bond or a bridging group selected from the bridges —O, —S, —NH— and —CH$_2$—.

Particularly preferred are compounds of general formula 1 wherein
- $X^-$ denotes an anion with a single negative charge selected from among the chloride, bromide and methanesulphonate, preferably bromide;
- A and B which may be identical or different, preferably identical, denote —S or —CH=CH—;
- R denotes hydrogen, hydroxy, methyl, ethyl, methyloxy, ethyloxy, —CF$_3$, or fluorine;

R$^1$ and R$^2$ which may be identical or different denote methyl, ethyl, —CH$_2$F or —CH$_2$—CH$_2$F, preferably methyl or ethyl;

R$^3$, R$^4$, R$^{3'}$ and R$^{4'}$, which may be identical or different, denote hydrogen, methyl, methyloxy, —CF$_3$ or fluorine;

R$^x$ and R$^{x'}$ which may be identical or different denote hydrogen, methyl, methyloxy, —CF$_3$ or fluorine or R$^x$ and R$^{x'}$ together denote a single bond or the bridging group —O—.

Of particular importance according to the invention are compounds of general formula 1 wherein X$^-$ denotes an anion with a single negative charge selected from among the chloride, bromide and methanesulphonate, preferably bromide;

A and B which may be identical or different, preferably identical, denote —S or —CH═CH—;

R denotes hydrogen, hydroxy or methyl, preferably hydroxy;

R$^1$ and R$^2$ which may be identical or different denote methyl or ethyl;

R$^3$, R$^4$, R$^{3'}$ and R$^{4'}$, which may be identical or different denote hydrogen, —CF$_3$ or fluorine, preferably hydrogen;

R$^x$ and R$^{x'}$ which may be identical or different denote hydrogen, —CF$_3$ or fluorine, preferably hydrogen or R$^x$ and R$^{x'}$ together denote a single bond or the bridging group —O, preferably a single bond.

Also preferred according to the invention are compounds of general formula 1 wherein X$^-$ denotes bromide;

A and B which may be identical or different, preferably identical, denote —S or —CH═CH—;

R denotes hydrogen, hydroxy or methyl, preferably hydroxy;

R$^1$ and R$^2$ denotes methyl;

R$^3$, R$^4$, R$^{3'}$ and R$^{4'}$, which may be identical or different, denote hydrogen or fluorine, preferably hydrogen;

R$^x$ and R$^{x'}$ which may be identical or different denote hydrogen or fluorine, preferably hydrogen or R$^x$ and R$^{x'}$ together denote a single bond or the bridging group —O, preferably a single bond.

The invention relates to the compounds of formula 1 optionally in the form of the individual optical isomers, mixtures of the individual enantiomers or racemates thereof and optionally in the form of the pharmacologically acceptable acid addition salts thereof.

In the compounds of general formula 1 the groups R$^3$, R$^4$, R$^{3'}$ and R$^{4'}$, if they do not represent hydrogen, may in each case be arranged in the ortho, meta or para position relative to the bond to the "—C—R" group. If none of the groups R$^3$, R$^4$, R$^{3'}$ and R$^{4'}$ denotes hydrogen, R$^3$ and R$^{3'}$ are preferably linked in the para position and R$^4$ and R$^{4'}$ are preferably linked in the ortho or meta position, most preferably in the meta position. If one of the groups R$^3$ and R$^4$ and one of the groups R$^{3'}$ and R$^{4'}$ denotes hydrogen, the other group in each case is preferably bonded in the meta or para position, most preferably in the para position. If none of the groups R$^3$, R$^4$, R$^{3'}$ and R$^{4'}$ denotes hydrogen, the compounds of general formula 1 wherein the groups R$^3$, R$^4$, R$^{3'}$ and R$^{4'}$ have the same meaning are particularly preferred according to the invention. Of particular importance according to the invention are the compounds of general formula 1 wherein A denotes —CH═CH— and B denotes —CH═CH—.

These compounds correspond to general formula 1'

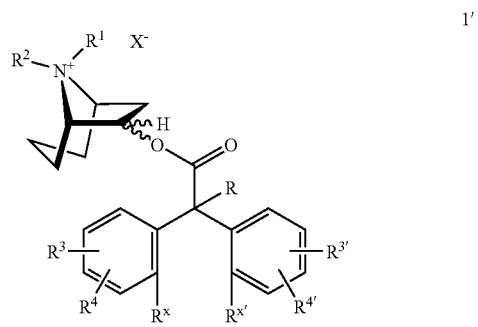

wherein X$^-$ and the groups R, R$^1$, R$^2$, R$^3$, R$^{3'}$, R$^4$, R$^{4'}$, R$^x$ and R$^{x'}$ may have the meanings given above.

Also of particular importance according to the invention are the compounds of general formula 1, wherein A denotes —S— and B denotes —S—. These compounds correspond to general formula 1"

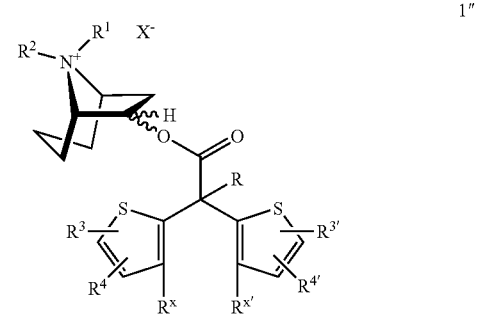

wherein X$^-$ and the groups R, R$^1$, R$^2$, R$^3$, R$^{3'}$, R$^4$, R$^{4'}$, R$^x$ and R$^{x'}$ may have the meanings given above.

The following compounds are particularly important according to the invention:

tropan-6exo-yl benzilate methobromide;

tropan-6exo-yl 9-hydroxy-fluorene-9-carboxylate methobromide;

tropan-6-exo-yl 2-hydroxy-2,2-dithiophene-acetate methobromide;

tropan-6exo-yl 9-hydroxy-xanthene-9-carboxylate methobromide;

tropan-6endo-yl benzilate methobromide;

tropan-6endo-yl 9-hydroxy-fluorene-9-carboxylate methobromide;

tropan-6endo-yl 9-hydroxy-xanthene-9-carboxylate methobromide;

tropan-6endo-yl 2-hydroxy-2,2-dithiophene-acetate methobromide.

The alkyl groups used, unless otherwise stated, are branched and unbranched alkyl groups having 1 to 4 carbon atoms. Examples include: methyl, ethyl, propyl or butyl. The groups methyl, ethyl, propyl or butyl may optionally also be referred to by the abbreviations Me, Et, Prop or Bu. Unless otherwise stated, the definitions propyl and butyl also include all possible isomeric forms of the groups in question. Thus, for example, propyl includes n-propyl and iso-propyl, butyl includes iso-butyl, sec. butyl and tert.-butyl, etc.

The cycloalkyl groups used, unless otherwise stated, are alicyclic groups with 3 to 6 carbon atoms. These are the cyclopropyl, cyclobutyl, cyclopentyl and cyclohexyl groups. According to the invention cyclopropyl is of particular importance within the scope of the present invention.

The alkylene groups used, unless otherwise stated, are branched and unbranched double-bonded alkyl bridges with 1 to 4 carbon atoms. Examples include: methylene, ethylene, propylene or butylene.

The alkylene-halogen groups used, unless otherwise stated, are branched and unbranched double-bonded alkyl bridges with 1 to 4 carbon atoms which may be mono-, di- or trisubstituted, preferably disubstituted, by a halogen. Accordingly, unless otherwise stated, the term alkylene-OH groups denotes branched and unbranched double-bonded alkyl bridges with 1 to 4 carbon atoms which may be mono-, di- or trisubstituted, preferably monosubstituted, by a hydroxy.

The alkyloxy groups used, unless otherwise stated, are branched and unbranched alkyl groups with 1 to 4 carbon atoms which are linked via an oxygen atom. The following may be mentioned, for example: methyloxy, ethyloxy, propyloxy or butyloxy. The groups methyloxy, ethyloxy, propyloxy or butyloxy may optionally also be referred to by the abbreviations MeO, EtO, PropO or BuO. Unless otherwise stated, the definitions propyloxy and butyloxy also include all possible isomeric forms of the groups in question. Thus, for example, propyloxy includes n-propyloxy and iso-propyloxy, butyloxy includes iso-butyloxy, sec. butyloxy and tert.-butyloxy, etc. The word alkoxy may also possibly be used within the scope of the present invention instead of the word alkyloxy. The groups methyloxy, ethyloxy, propyloxy or butyloxy may optionally also be referred to as methoxy, ethoxy, propoxy or butoxy.

The alkylene-alkyloxy groups used, unless otherwise stated, are branched and unbranched double-bonded alkyl bridges with 1 to 4 carbon atoms which may be mono-, di- or trisubstituted, preferably monosubstituted, by an alkyloxy group.

The —O—CO-alkyl groups used, unless otherwise stated, are branched and unbranched alkyl groups with 1 to 4 carbon atoms which are bonded via an ester group. The alkyl groups are bonded directly to the carbonylcarbon of the ester group. The term —O—CO-alkyl-halogen group should be understood analogously. The group —O—CO—CF$_3$ denotes trifluoroacetate.

Within the scope of the present invention halogen denotes fluorine, chlorine, bromine or iodine. Unless otherwise stated, fluorine and bromine are the preferred halogens. The group CO denotes a carbonyl group.

As explained hereinafter, the compounds according to the invention may be prepared partly analogously to the methods already known in the art (Diagram 1).

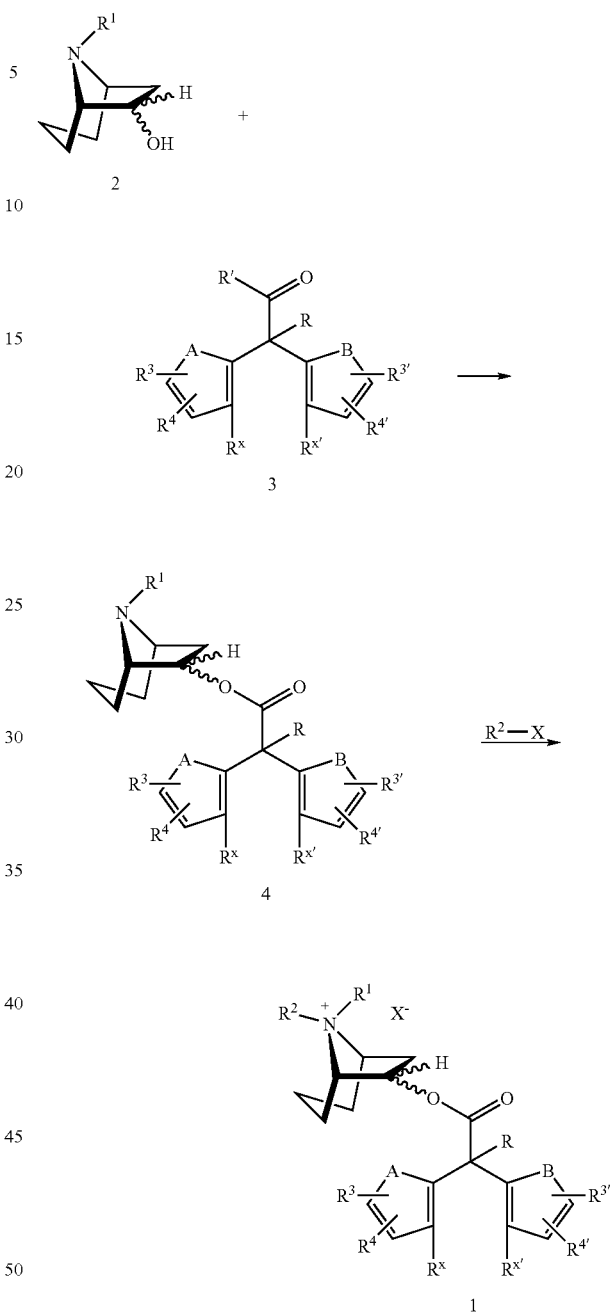

Diagram 1:

The carboxylic acid derivatives of formula 3 are known in the art or may be obtained by methods of synthesis known in the art. If only suitably substituted carboxylic acids are known in the art, the compounds of formula 3 may also be obtained directly from them by acid- or base-catalysed esterification with the corresponding alcohols or by halogenation with the corresponding halogenation reagents.

Starting from the compounds of formula 2 the esters of general formula 4 may be obtained by reaction with the carboxylic acid derivatives of formula 3, wherein R' denotes for example chlorine or a $C_1$-$C_4$-alkyloxy group. When R' equals $C_1$-$C_4$-alkyloxy this reaction may be carried out for example in a sodium melt at elevated temperature, preferably at about 50-150° C., more preferably at about 90-100° C. at low pressure, preferably at below 500 mbar, most preferably at below 75 mbar. Alternatively, instead of the derivatives 3 wherein R' denotes $C_1$-$C_4$-alkyloxy, the corresponding acid chlorides (R=Cl) may also be used.

The compounds of formula 4 thus obtained may be converted into the target compounds of formula 1 by reacting with the compounds $R^2$—X, wherein $R^2$ and X may have the abovementioned meanings. This synthesis step may also be carried out analogously to the examples of synthesis disclosed in WO 92/16528. In the case wherein $R^1$ and $R^2$ together form an alkylene bridge there is no need to add the reagent $R^2$—X, as will be apparent to the skilled man. In this case the compounds of formula 4 contain a suitably substituted group $R^1$ (for example —$C_3$-$C_5$-alkylene-halogen) according to the above definitions and the compounds of formula 1 are prepared by intramolecular quaternisation of the amine.

Alternatively, the compounds of formula 4 wherein R denotes halogen may also be prepared by the method shown in Diagram 2.

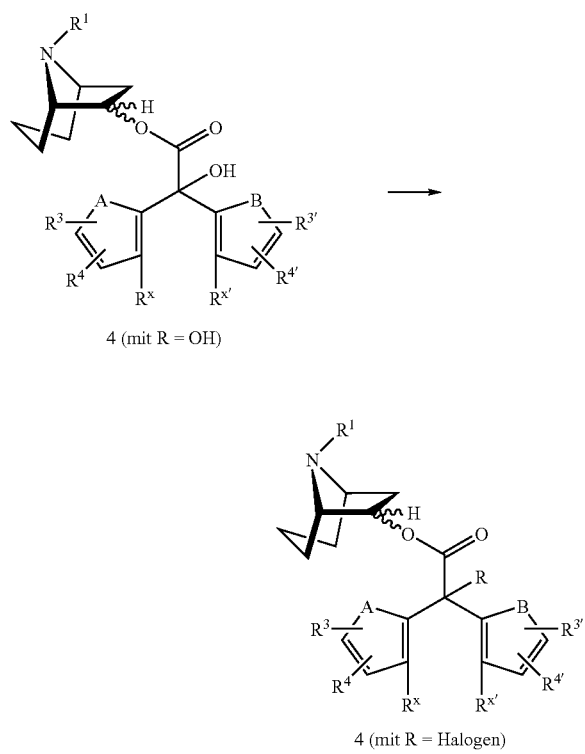

Diagram 2:

For this, the compounds of formula 4 wherein R denotes hydroxy are converted into the compounds 4 wherein R denotes halogen using suitable halogenation reagents. The method used for the halogenation reactions to be carried out according to Diagram 2 is sufficiently well known in the art.

As is apparent from Diagram 1, the intermediate products of general formula 4 have a central importance. Accordingly, in another aspect, the present invention relates to the intermediates of formula 4

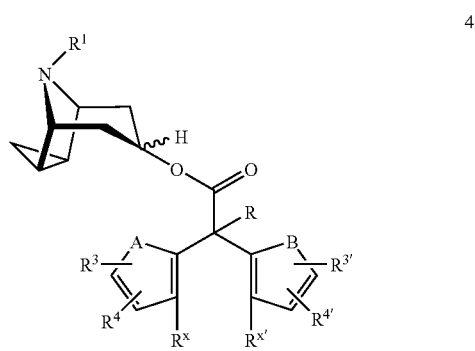

wherein the groups A, B, R, $R^1$, $R^3$, $R^{3'}$, $R^4$, $R^{4'}$, $R^x$ and $R^{x'}$ may be defined as above, optionally in the form of the acid addition salts thereof. By acid addition salts are meant salts selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate.

As in the compounds of general formula 1 the groups $R^3$, $R^4$, $R^{3'}$ and $R^{4'}$, if they do not represent hydrogen, may in each case be arranged in the ortho, meta or para position relative to the bond to the "—C—R" group in the compounds of general formula 4 as well. If none of the groups $R^3$, $R^4$, $R^{3'}$ and $R^{4'}$ denotes hydrogen, $R^3$ and $R^{3'}$ are preferably linked in the para position and $R^4$ and $R^{4'}$ are preferably linked in the ortho or meta position, most preferably in the meta position. If one of the groups $R^3$ and $R^4$ and one of the groups $R^{3'}$ and $R^{4'}$ denotes hydrogen, the other group in each case is preferably linked in the meta or para position, most preferably in the para position. If none of the groups $R^3$, $R^4$, $R^{3'}$ and $R^{4'}$ denotes hydrogen the compounds of general formula 4 which are particularly preferred according to the invention are those wherein the groups $R^3$, $R^4$, $R^{3'}$ and $R^{4'}$ have the same meaning.

As is apparent from Diagram 1, the compounds of formula 2 are used as starting products for preparing the compounds of formula 1. These compounds are partly known in the prior art (Jones, J. Chem. Soc 1959, 615; D. E. Justice, THL 1995 4689-4692). Accordingly, in another aspect, the present invention relates to the as yet unknown use of the compounds of general formula 2

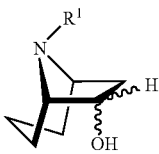

wherein

R[1] denotes hydrogen or —$C_1$-$C_5$-alkyl, which may optionally be substituted by —$C_3$-$C_6$-cycloalkyl, hydroxy or halogen, optionally in the form of the acid addition salts thereof, for preparing the compounds of general formula 4.

By the acid addition salts are meant salts selected from among the hydrochloride, hydrobromide, sulphate, phosphate, fumarate and methanesulphonate.

It is preferable to use the abovementioned compounds of general formula 2 wherein R[1] denotes hydrogen or $C_1$-$C_4$-alkyl, which may optionally be substituted by hydroxy, fluorine, chlorine or bromine, optionally in the form of the acid addition salts thereof.

It is particularly preferred to use the abovementioned compounds of general formula 2 wherein R[1] denotes hydrogen, methyl, ethyl, —$CH_2F$ or —$CH_2$—$CH_2F$, preferably methyl or ethyl, optionally in the form of the acid addition salts thereof.

Of particular importance according to the invention is the abovementioned use of compounds of general formula 2 wherein R[1] denotes hydrogen, methyl or ethyl, optionally in the form of the acid addition salts thereof.

Also preferred according to the invention is the abovementioned use of compounds of general formula 2 wherein R[1] denotes hydrogen or methyl, optionally in the form of the acid addition salts thereof.

Moreover, the present invention relates to the use of the abovementioned compounds of general formula 2 as starting materials for preparing the compounds of general formula 1.

The examples of synthesis described below serve to illustrate the present invention still further. However, they are to be regarded as only examples of the procedure, as further illustration of the invention, without restricting the invention to the object described below by way of example.

Preparation of the Bases 2a and 2b:

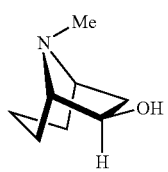

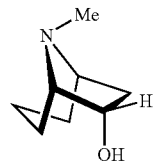

The compounds of formula 2a and 2b may be prepared by methods known in the art (cf. Jones, J. Chem. Soc 1959, 615; D. E. Justice, THL 1995 4689-4692).

EXAMPLE 1

Tropan-6exo-yl benzilate methobromide

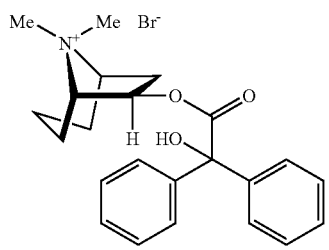

1.1.: methyl benzilate 3a:.

90 g (0.394 mol) benzilic acid are dissolved in 900 ml acetonitrile and at 5° C. 109.6 g (0.72 mol) of DBU are added dropwise. After the addition of 204.4 g (1.44 mol) of methyl iodide the mixture is stirred for 24 hours at ambient temperature (about 20-23° C.). The solution is evaporated down to the residue, the residue is taken up in diethyl ether and extracted with water. The organic phase is washed with 5% aqueous sodium carbonate solution and water, dried and the solvent is distilled off. The product is purified by recrystallisation from cyclohexane. Yield: 77.19 g white crystals (=81% of theory) Melting point: 74°-76° C.

1.2.: Tropan-6exo-yl benzilate 4a:

1.2 g of compound 2a are combined with 2.42 g of methyl benzylate 3a and 10 mg of sodium and heated to 100° C. for 1 h at 70 mbar. The mixture is cooled and 10 ml acetonitrile are added to decompose any excess sodium. Then the solvent is distilled off under reduced pressure. The residue remaining is combined with 100 ml of toluene and washed 1× with 100 nm of water. The organic phase is dried and the solvent distilled off under reduced pressure. The product is purified by chromatography on silica gel (about 100 ml silica gel; 150 ml ethyl acetate, then about 500 ml of a solvent mixture consisting of dichloromethane 70: ethyl acetate 20: methanol 10). Yield: 2.2 g (74%); Melting point: 135° C.

1.3: Tropan-6exo-yl benzilate methobromide:

2.1 g of compound 4a are dissolved in 40 mL acetonitrile and 40 mL dichloromethane and combined with 3.42 g of a 50% solution of methyl bromide in acetonitrile. The mixture is stirred for 24 h at RT (ambient temperature) and the crystals precipitated are suction filtered and washed with diethyl ether. Yield: 2.4 g (90%); Melting point: 264° C.

EXAMPLE 2 tropan-6exo-yl 9-hydroxy-fluorene-9-carboxylate methobromide

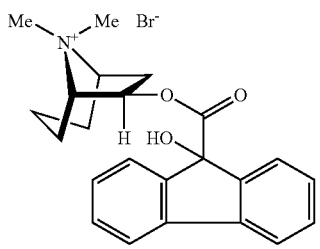

2.1.: methyl 9-hydroxy-fluorene-9-carboxylate 3b:.

50.4 g (0.223 mol) 9-hydroxy-9-fluorenecarboxylic acid are dissolved in 500 ml of methanol, combined with 5 ml (0.089 mol) conc. sulphuric acid and refluxed for 1 hour. After cooling 100 ml sodium hydrogen carbonate solution (about pH 8) are added, and the methanol is largely distilled off under reduced pressure. The residue remaining is extracted with dichloromethane and water, the organic phase is dried and evaporated to dryness.

The product is purified by recrystallisation from ethyl acetate.

Yield: 50.0 g (=93% d. Th.)

2.2: tropan-6exo-yl 9-hydroxy-fluorene-9-carboxylate 4b:

1.05 g 2a, 2.4 g methyl fluorenehydroxycarboxylate 3b and 10 mg sodium are stirred for 1 h at 100° C. and 70 mbar. The mixture is cooled and 10 ml of acetonitrile are added to break down excess sodium. Then the solvent is distilled off under reduced pressure. The residue is combined with 100 ml of toluene and washed 1× with 100 ml of water. The organic phase is dried, the solvent distilled off under reduced pressure and the residue purified by chromatography (about 100 ml silica gel; 150 ml ethyl acetate, then about 500 ml a solvent mixture consisting of dichloromethane 70: ethyl acetate 20: methanol 10). Yield: 1.1 g (44%); melting point 154° C.

2.3: tropan-6exo-yl 9-hydroxy-fluorene-9-carboxylate methobromide:

1.1 g 4b are dissolved in 20 mL acetonitrile and 20 mL dichloromethane, combined with 1.82 g of a 50% solution of methylbromide in acetonitrile and stirred for 24 h at RT. Then the solvent is distilled off under reduced pressure and the residue is taken up in 5 mL methanol and combined with 30 mL acetone. After 2 h the crystals precipitated are suction filtered. Yield: 0.7 g (50%); Melting point: >300° C. (decomposition).

EXAMPLE 3 tropan-6-exo-yl 2-hydroxy-2,2-dithiophene-acetate methobromide

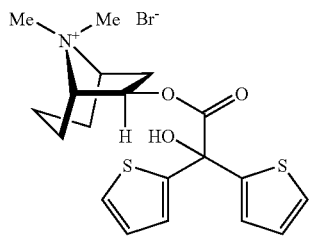

3.1: tropan-6-exo-yl 2-hydroxy-2,2-dithiophene-acetate 4c:

1.05 g 2a, 2.54 g methyl dithienylglycolate 3c and 10 mg of sodium are stirred for 1 h at 100° C. and 70 mbar. The mixture is cooled and 10 ml of acetonitrile are added to break down excess sodium. Then the solvent is distilled off under reduced pressure. The residue is combined with 100 ml of toluene and washed 1× with 100 ml of water. The organic phase is dried and the solvent distilled off under reduced pressure. The residue is purified by chromatography on silica gel (about 100 ml silica gel; 150 ml ethyl acetate, then about 500 ml of a solvent mixture consisting of dichloromethane 70: ethyl acetate 20: methanol 10). Yield 0.9 g (35%);

Melting point: 141° C.

3.2: tropan-6-exo-yl 2-hydroxy-2,2-dithiophen-acetate methobromide:

0.9 g 4c are dissolved in 20 mL acetonitrile and 20 mL dichloromethane, combined with 1.42 g of a 50% solution of methylbromide in acetonitrile and stirred for 24 h at RT. The crystals precipitated are suction filtered and washed with ether. Yield: 0.9 g (79%);

Melting point: 220° C. (decomposition).

EXAMPLE 4 tropan-6exo-yl 9-hydroxy-xanthene-9-carboxylate methobromide

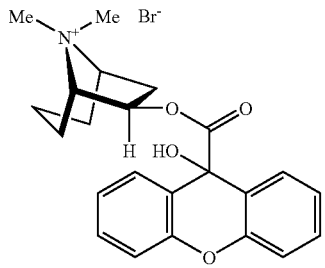

4.1.: methyl 9-hydroxy-xanthene-9-carboxylate 3d:.

a) methyl xanthene-9-carboxylate:

A sodium ethoxide solution is generated from 21.75 g (0.95 mol) of sodium and 1500 ml of ethanol. 214 g (0.95 mol) of xanthene-9-carboxylic acid is added batchwise to this solution and the suspension obtained is stirred for 1 hour at ambient temperature. Then the solid is separated off, washed with 1500 ml diethyl ether, the crystals isolated are suspended in 1500 ml of dimethylformamide and combined with 126.73 ml (2.0 mol) methyl iodide with stirring. The solution formed is left to stand for 24 hours at ambient temperature, then diluted with water to a total volume of 6 l, crystallised, suction filtered, washed with water and dried. Yield: 167 g of white crystals 7 (=74% of theory)

Melting point: 82° C.

b) methyl 9-hydroxy-xanthene-9-carboxylate 3d:

48.05 g (0.2 mol) methyl xanthene-9-carboxylate are dissolved in 1200 ml of tetrahydrofuran and at 0° C. 23.63 g (0.2 mol) of potassium tert. butoxide are added. Then oxygen is piped in for 2 hours at −10° to −5° C., the mixture is acidified with 2 N aqueous hydrochloric acid and the majority of the solvent is distilled off. The residue remaining is extracted with ethyl acetate and water, the organic phase is extracted with aqueous $Na_2S_2O_5$ solution, washed with water, dried and the solvent is distilled off. The product is purified by crystallisation from diisopropylether and cyclohexane. Yield: 11.10 g of white crystals (=22% of theory)

4.2: tropan-6exo-yl 9-hydroxy-xanthene-9-carboxylate 4d:

0.705 g 2a, 2.60 g methyl 9-hydroxy-xanthene-9-carboxylate 3d and 10 mg sodium are stirred for 2 h at 100° C. and 70 mbar. The mixture is cooled and 10 ml of acetonitrile are added to break down excess sodium. Then the solvent is distilled off under reduced pressure. The residue is combined with 100 ml of toluene and washed 1× with 100 ml of water. The organic phase is dried and the solvent distilled off under reduced pressure. The residue is purified by chromatography (about 100 ml silica gel; 150 ml ethyl acetate, then about 500 ml of a solvent mixture consisting of dichloromethane 70: ethyl acetate 20:methanol 10). Yield 0.45 g (25%); amorphous solid.

4.3: tropan-6exo-yl 9-hydroxy-xanthene-9-carboxylate methobromide 0.45 g of 4d are dissolved in 4.5 mL acetonitrile, combined with 0.50 g of a 50% solution of methylbromide in acetonitrile and stirred for 24 h at RT. The crystals precipitated are suction filtered and washed with ether. Yield 0.3 g (53%); Melting point: 255° C.

EXAMPLE 5

Tropan-6endo-yl benzilate methobromide

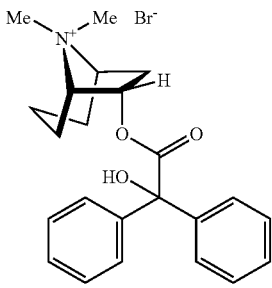

5.1.: methyl benzilate 3a:.

Prepared according to step 1.1.

5.2.: Tropan-6endo-yl benzilate 4e:

0.6 g 2b and 1.6 g methyl benzilate 3a are dissolved in 10 mL toluene and combined with 20 mg NaH. The mixture is heated to 140° C. while the methanol formed is distilled off. After 2 h it is cooled, 20 ml of water are added, the organic phase is separated off and extracted 2× with 30 ml of 1N hydrochloric acid. The aqueous phase is combined with potassium carbonate and extracted 2× with 30 ml dichloromethane. The combined organic phases are dried, the solvent distilled off under reduced pressure and the residue is crystallised from acetone with ethereal HCl (saturated). Yield: 1.2 g; Melting point: 265° C.

5.3: Tropan-6endo-yl benzilate methobromide:

1.2 g 4e are dissolved in 50 ml of water, combined with potassium carbonate and extracted 2× with 30 ml of dichloromethane. The organic phase is dried and distilled off under reduced pressure. The residue is taken up in 5 mL acetonitrile and combined with 0.5 g of a 50% solution of methylbromide in acetonitrile. The mixture is stirred for 24 h at RT, the crystals precipitated are suction filtered and washed with acetone and ether. Yield 1.0 g (66%); Melting point: 229° C.

EXAMPLE 6 tropan-6endo-yl 9-hydroxy-fluorene-9-carboxylate methobromide

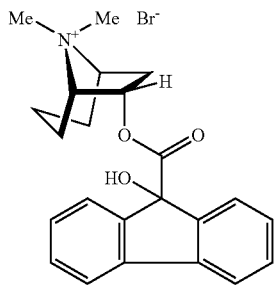

6.1.: methyl 9-hydroxy-fluorene-9-carboxylate 3b:.

Prepared as in step 2.1.

6.2: tropan-6endo-yl 9-hydroxy-fluorene-9-carboxylate 4f:

0.6 g 2b and 1.6 g methyl 9-hydroxy-fluorene-9-carboxylate 3b are dissolved in 10 mL toluene and combined with 20 mg NaH. The mixture is heated to 140° C. while the methanol formed is distilled off. After 2 h it is cooled, 20 ml of water are added, the organic phase is separated off and extracted 2× with 30 ml of 1N hydrochloric acid. The aqueous phase is combined with potassium carbonate and extracted 2× with 30 ml of dichloromethane. The combined organic phase is dried, the solvent is distilled off under reduced pressure and the residue is crystallised from acetone with saturated ethereal HCl. Yield: 1.2 g (73%); Melting point: 261° C.

6.3: tropan-6endo-yl 9-hydroxy-fluorene-9-carboxylate methobromide:

1.2 g of 4f are dissolved in 50 ml of water, combined with potassium carbonate and extracted 2× with 30 ml of dichloromethane. The organic phase is dried and the solvent is distilled off under reduced pressure. The residue is taken up in 5 mL acetonitrile and combined with 0.5 g of a 50% solution of methylbromide in acetonitrile. The mixture is stirred for 24 h at RT, the crystals precipitated are separated off and washed with acetone and ether. Yield: (70%).

EXAMPLE 7 tropan-6endo-yl9-hydroxy-xanthene-9-carboxylate methobromide

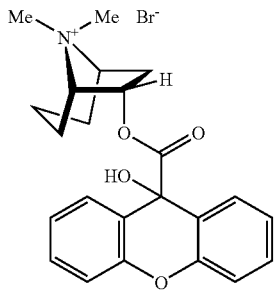

7.1.: methyl 9-hydroxy-xanthene-9-carboxylate 3d:.
Prepared as in step 4.1.

7.2: tropan-6endo-yl 9-hydroxy-xanthene-9-carboxylate 4g:
0.6 g of 2b and 1.6 g of methyl 9-hydroxy-xanthene-9-carboxylate 3d are dissolved in 10 mL toluene and combined with 20 mg NaH. The mixture is heated to 140° C. while the methanol formed is distilled off. After 2 h it is cooled, 20 ml of water are added, the organic phase is separated off and extracted 2× with 30 ml of 1N hydrochloric acid. The aqueous phase is combined with potassium carbonate and extracted 2× with 30 ml of dichloromethane. The combined organic phase is dried, the solvent is distilled off under reduced pressure and the residue is crystallised from acetone with saturated ethereal HCl. Yield: 1.1 g (73%); Melting point: 212° C.

7.3: tropan-6endo-yl 9-hydroxy-xanthene-9-carboxylate methobromide:
1.1 g of 4 are dissolved in 50 ml of water, combined with potassium carbonate and extracted 2× with 30 ml dichloromethane. The organic phase is dried and the solvent distilled off under reduced pressure. The residue is taken up in 5 mL acetonitrile and combined with 0.5 g of a 50% solution of methylbromide in acetonitrile. The mixture is stirred for 24 h at RT, the crystals precipitated are separated off and washed with acetone and ether. Yield: 1.0 g (72%); Melting point: 250° C.

EXAMPLE 8 tropan-6endo-yl 2-hydroxy-2,2-dithiophene-acetate methobromide

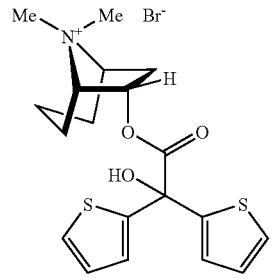

8.1: tropan-6endo-yl 2-hydroxy-2,2-dithiophene-acetate 4h:
0.6 g 2b and 1.7 g methyl di-(2-thienyl)glycolate 3c are dissolved in 10 mL toluene and combined with 20 mg NaH. The mixture is heated to 140° C. while the methanol formed is distilled off. After 2 h it is cooled, 20 ml of water are added, the organic phase is separated off and extracted 2× with 30 ml of 1N hydrochloric acid. The aqueous phase is combined with potassium carbonate and extracted 2× with 30 ml dichloromethane. The combined organic phase is dried, the solvent is distilled off under reduced pressure and the residue is crystallised from acetone by means of saturated ethereal HCl. Yield: 1.1 g (65%);
Melting point: 242° C.

8.2: tropan-6endo-yl 2-hydroxy-2,2-dithiophene-acetate methobromide:
1.1 g 4 h are dissolved in 50 ml of water, combined with potassium carbonate and extracted 2× with 30 ml dichloromethane. The organic phase is dried and the solvent is distilled off under reduced pressure. The residue is taken up in 5 mL acetonitrile and combined with 0.5 g of a 50% solution of methylbromide in acetonitrile. The mixture is stirred for 24 h at RT, the crystals precipitated are separated off and washed with acetone and ether. Yield: 1.1 g (79%); Melting point: 218° C.

It was found that the compounds according to the invention of formula 1 are antagonists of the M3 receptor (Muscarinic Receptor subtype 3). The compounds according to the invention have Ki values of less than 100 nM in terms of their affinity for the M3 receptor. These values were determined by the method described below.

Chemicals

3H-NMS was obtained from Messrs Amersham of Braunschweig, with a specific radioactivity of 3071 GBq/mmol (83 Ci/mmol). All the other reagents were obtained from Serva of Heidelberg and Merck of Darmstadt.

Cell Membranes:

We used cell membranes from CHO (Chinese hamster ovary) cells which were transfected with the corresponding genes of the human muscarinic receptor subtypes hm1 to hm5 (BONNER). The cell membranes of the desired subtype were thawed, resuspended by hand with a glass homogeniser and diluted with HEPES buffer to a final concentration of 20-30 mg of protein/ml.

Receptor Binding Studies:

The binding assay was carried out in a final volume of 1 ml and consisted of 100 µl of unlabelled substance in various concentrations, 100 µl of radioligand (3H—N-methylscopolamine 2 nmol/L (3H-NMS), 200 µl of membrane preparation and 600 µl of HEPES buffer (20 mmol/L HEPES, 10 mmol/L $MgCl_2$, 100 mmol/L NaCl, adjusted with 1 mol/L NaOH to pH 7.4).

The nonspecific binding was determined using 10 µmol/l of atropine.

The preparation was incubated for 45 min. at 37° C. in 96-well microtitre plates (Beckman, polystyrene, No. 267001) as a double measurement. The incubation was ended by filtering using an Inotech Cell Harvester (type IH 110) through Whatman G-7 filters. The filters were washed with 3 ml of ice-cooled HEPES buffer and dried before measuring.

Determining the Radioactivity:

The radioactivity of the filter mats was measured simultaneously using a two-dimensional digital autoradiograph (Berthold, Wildbad, type 3052).

Evaluation:

The Ki values were calculated using implicit equations which were derived directly from the mass-action law, with the model for the 1 receptor 2 ligand reaction (SysFit software, SCHITTKOWSKI).

Literature:

BONNER TI, New subtypes of muscarinic acetylcholine receptors Trends Pharmacol. Sci. 10, Suppl.: 11-15 (1989); SCHITTKOWSKI K Parameter estimation in systems of nonlinear equations Numer Math. 68: 129-142 (1994).

The compounds of formula 1 according to the invention are characterised by their range of uses in the therapeutic field. Particular mention should be made of those applications for which the compounds of formula 1 according to the invention may preferably be used on the basis of their pharmaceutical activity as anticholinergics.

These are for example the treatment of asthma or COPD (chronic obstructive pulmonary disease). The compounds of general formula 1 may also be used to treat vagally induced sinus bradycardia and to treat heart rhythm disorders. Generally, the compounds according to the invention may also be used therapeutically to treat spasms, for example, in the gastrointestinal tract. They may also be used to treat spasms in the urinary tract and also to treat menstrual pain, for example. Of the ranges of indications mentioned above, the treatment of asthma and COPD with the compounds of formula 1 according to the invention is of particular importance.

The compounds of general formula 1 may be used on their own or in conjunction with other active substances of formula 1. The compounds of general formula 1 may also be used in combination with other pharmacologically active substances. These may be, in particular, betamimetics, antiallergics, dopamine agonists, PAF antagonists, PDE-IV inhibitors, leukotriene antagonists, p38 kinase inhibitors, EGFR kinase inhibitors and corticosteroids as well as combinations of active substances thereof.

Examples of betamimetics which may be used according to the invention in conjunction with the compounds of formula 1 include compounds selected from among bambuterol, bitolterol, carbuterol, clenbuterol, fenoterol, formoterol, hexoprenaline, ibuterol, pirbuterol, procaterol, reproterol, salmeterol, sulphonterol, terbutaline, tolubuterol, 4-hydroxy-7-[2-{[2-{[3-(2-phenylethoxy)propyl]sulphonyl}ethyl]-amino}ethyl]-2(3H)- benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluormethylphenyl)-2-tert.-butylamino)ethanol and 1-(4-ethoxycarbonylamino-3-cyano-5-fluorophenyl)-2-(tert.-butylamino)ethanol, optionally in the form of the racemates, the enantiomers, the diastereomers and optionally the pharmacologically acceptable acid addition salts, the solvates and/or the hydrates thereof. Most preferably, the betamimetics used as active substances in conjunction with the compounds of formula 1 according to the invention are selected from among fenoterol, formoterol, salmeterol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino)}ethanol, optionally in the form of the racemates, the enantiomers, the diastereomers and optionally the pharmacologically acceptable acid addition salts and the hydrates thereof. Of the betamimetics mentioned above the compounds formoterol and salmeterol are particularly preferred, optionally in the form of the racemates, the enantiomers, the diastereomers and optionally the pharmacologically acceptable acid addition salts thereof, and the hydrates thereof. According to the invention, the acid addition salts of the betamimetics selected, for example, from among the hydrochloride, hydrobromide, sulphate, phosphate, fumarate, methanesulphonate and xinafoate are preferred. Particularly preferred in the case of salmeterol are the salts selected from among the hydrochloride, sulphate and xinafoate, of which the xinafoate is particularly preferred. Particularly preferred in the case of formoterol are the salts selected from among the hydrochloride, sulphate and fumarate, of which the hydrochloride and fumarate are particularly preferred. According to the invention, formoterol fumarate is of exceptional importance.

Within the scope of the present invention, the corticosteroids which may optionally be used in conjunction with the compounds of formula 1 may be compounds selected from among flunisolide, beclomethasone, triamcinolone, budesonide, fluticasone, mometasone, ciclesonide, rofleponide, GW 215864, KSR 592, ST-126 and dexamethasone. Preferably, within the scope of the present invention, the corticosteroids are selected from among flunisolide, beclomethasone, triamcinolone, budesonide, fluticasone, mometasone, ciclesonide and dexamethasone, while budesonide, fluticasone, mometasone and ciclesonide are important and budesonide and fluticasone are particularly important. In some cases, within the scope of the present patent application, the term steroids is used on its own instead of the word corticosteroids. Any reference to steroids within the scope of the present invention includes a reference to salts or derivatives which may be formed from the steroids. Examples of possible salts or derivatives include: sodium salts, sulphobenzoates, phosphates, isonicotinates, acetates, propionates, dihydrogen phosphates, palmitates, pivalates or furoates. In some cases the corticosteroids may also occur in the form of their hydrates.

Examples of PDE-IV inhibitors which may be used according to the invention as a combination with the compound of formula 1 include compounds selected from among enprofylline, roflumilast, ariflo, Bay-198004, CP-325,366, BY343, D-4396 (Sch-351591), V-11294A and AWD-12-281. Preferred PDE-IV inhibitors are selected from among enprofylline, roflumilast, ariflo and AWD-12-281, while AWD-12-281 is particularly preferred as the combination partner with the compound of formula 1 according to the invention. Any reference to the abovementioned PDE-IV inhibitors also includes, within the scope of the present invention, a reference to any pharmacologically acceptable acid addition salts thereof which may exist. By the physiologically acceptable acid addition salts which may be formed by the abovementioned PDE-IV inhibitors are meant, for example, pharmaceutically acceptable salts selected from among the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid. According to the invention, the salts selected from among the acetate, hydrochloride, hydrobromide, sulphate, phosphate and methanesulphonate are preferred in this context.

Within the scope of the present invention, the term dopamine agonists, which may optionally be used in conjunction with the compounds of formula 1, denotes compounds selected from among bromocriptine, cabergolin, alpha-dihydroergocryptine, lisuride, pergolide, pramipexol, roxindol, ropinirol, talipexol, tergurid and viozan. It is preferable within the scope of the present invention to use, as combination partners with the compounds of formula 1, dopamine agonists selected from among pramipexol, talipexol and viozan, pramipexol being of particular importance. Any reference to the abovementioned dopamine agonists also includes, within the scope of the present invention, a reference to any pharmacologically acceptable acid addition salts and hydrates thereof which may exist. By the physiologically acceptable acid addition salts thereof which may be formed by the abovementioned dopamine agonists are meant, for example, pharmaceutically acceptable salts selected from among the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of antiallergic agents which may be used according to the invention as a combination with the compound of formula 1 include epinastin, cetirizin, azelastin, fexofenadin, levocabastin, loratadine, mizolastin, ketotifen, emedastin, dimetinden, clemastine, bamipin, cexchlorpheniramine, pheniramine, doxylamine, chlorphenoxamine, dimenhydrinate, diphenhydramine, promethazine, ebastin, desloratidine and meclizine. Preferred antiallergic agents which may be used within the scope of the present invention in combination with the compounds of formula 1 according to the invention are selected from among epinastin, cetirizin, azelastin, fexofenadin, levocabastin, loratadine, ebastin, desloratidine and mizolastin, epinastin and desloratidine being particularly preferred. Any reference to the abovementioned antiallergic agents also includes, within the scope of the present invention, a reference to any pharmacologically acceptable acid addition salts thereof which may exist.

Examples of PAF antagonists which may be used according to the invention as a combination with the compounds of formula 1 include 4-(2-chlorophenyl)-9-methyl-2-[3-(4-morpholinyl)-3-propanon-1-yl]-6H-thieno-[3,2-f][1,2,4]triazolo[4.3-a][1,4]diazepine, 6-(2-chlorophenyl)-8,9-dihydro-1-methyl-8-[(4-morpholinyl)carbonyl]-4H,7H-cyclopenta-[4.5]thieno-[3,2-f][1,2,4]triazolo[4,3-a][1,4]diazepine.

Examples of EGFR kinase inhibitors which may be used as a combination with the compounds of formula 1 according to the invention include, in particular, 4-[(3-chloro-4-fluorophenyl)amino]-7-[4-((R)-6-methyl-2-oxo-morpholin-4-yl)-butyloxy]-6-[(vinylcarbonyl)amino]-quinazoline, 4-[(3-chloro-4-fluoro-phenyl)amino]-7-[4-((S)-6-methyl-2-oxo-morpholin-4-yl)-butyloxy]-6-[(vinylcarbonyl)amino]-quinazoline, 4-[(3-chloro-4-fluoro-phenyl)amino]-7-(2-{4-[(S)-(2-oxo-tetrahydrofuran-5-yl)carbonyl]-piperazin-1-yl}-ethoxy)-6-[(vinylcarbonyl)amino]-quinazoline, 4-[(3-chloro-4-fluoro-phenyl)amino]-7-[2-((S)-6-methyl-2-oxo-morpholin-4-yl)-ethoxy]-6-[(vinylcarbonyl)amino]-quinazoline, 4-[(3-chloro-4-fluorophenyl)amino]-6-[(4-{N-[2-(ethoxycarbonyl)-ethyl]-N-[(ethoxycarbonyl)methyl]amino}-1-oxo-2-buten-1-yl)amino]-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopropylmethoxy-quinazoline and 4-[(3-chloro-4-fluorophenyl)amino]-6-[3-(morpholin-4-yl)-propyloxy]-7-methoxy-quinazoline. Any reference to the abovementioned EGFR kinase inhibitors also includes, within the scope of the present invention, a reference to any pharmacologically acceptable acid addition salts thereof which may exist. By the physiologically or pharmacologically acceptable acid addition salts thereof which may be formed by the EGFR kinase inhibitors are meant, according to the invention, pharmaceutically acceptable salts selected from among the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid. The salts of the EGFR kinase inhibitors selected from among the salts of acetic acid, hydrochloric acid, hydrobromic acid, sulphuric acid, phosphoric acid and methanesulphonic acid are preferred according to the invention.

Particularly preferred examples of p38 kinase inhibitors which may be used as a combination with the compounds of formula 1 according to the invention include 1-[5-tert-butyl-2-p-tolyl-2H-pyrazol-3-yl]-3-[4-(2-morpholin-4-yl-ethoxy)naphthalin-1-yl]-urea; 1-[5-tert-butyl-2-p-tolyl-2H-pyrazol-3-yl]-3-[4-(2-(1-oxothiomorpholin-4-yl)ethoxy)naphthalin-1-yl]-urea; 1-[5-tert-butyl-2-(2-methylpyridin-5-yl)-2H-pyrazol-3-yl]-3-[4-(2-pyridine-4-yl-ethoxy)naphthalin-1-yl]-urea; 1-[5-tert-butyl-2-(2-methoxypyridin-5-yl)-2H-pyrazol-3-yl]-3-[4-(2-morpholin-4-yl-ethoxy)naphthalin-1-yl]-urea or 1-[5-tert-butyl-2-methyl-2H-pyrazol-3-yl]-3-[4-(2-morpholin-4-yl-ethoxy)naphthalen-1-yl]-urea. Any reference to the abovementioned p38 kinase inhibitors also includes, within the scope of the present invention, a reference to any pharmacologically acceptable acid addition salts thereof which may exist. By the physiologically or pharmacologically acceptable acid addition salts thereof which may be formed by the p38 kinase inhibitors are meant, according to the invention, pharmaceutically acceptable salts selected from among the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

If the compounds of formula 1 are used in conjunction with other active substances, the combination with steroids, PDE IV inhibitors or betamimetics is particularly preferred, of the categories of compounds mentioned above. The combination with betamimetics, particularly with long-acting betamimetics, is of particular importance. The combination of the compounds of formula 1 according to the invention with salmeterol or formoterol is particularly preferred.

Suitable preparations for administering the salts of formula 1 include for example tablets, capsules, suppositories and solutions, etc. Administration of the compounds according to the invention by inhalation is of particular importance according to the invention (particularly for treating asthma or COPD). The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilisers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatin and the like. Lubricants such as magnesium stearate, sodium laurylsulphate and talc may also be used to produce the tablets. In the case of aqueous suspensions the active substances may be combined with various flavour enhancers or colourings in addition to the abovementioned excipients.

For administering the compounds of formula 1 for the treatment of asthma or COPD it is particularly preferred according to the invention to use preparations or pharmaceutical formulations which are suitable for inhalation. Inhalable preparations include inhalable powders, propellant-containing metering aerosols or propellant-free inhalable solutions Within the scope of the present invention, the term propellant-free inhalable solutions also includes concentrates or sterile inhalable solutions ready for use. The formulations which may be used within the scope of the present invention are described in more detail in the next part of the specification The inhalable powders which may be used according to the invention may contain 1 either on their own or in admixture with suitable physiologically acceptable excipients.

If the active substances 1 are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 µm, preferably between 10 and 150 µm, most preferably between 15 and 80 µm. It may sometimes seem appropriate to add finer excipient fractions with an average particle size of 1 to 9 µm to the excipient mentioned above. These finer excipients are also selected from the group of possible excipients listed hereinbefore. Finally, in order to prepare the inhalable powders according to the invention, micronised active substance 1, preferably with an average particle size of 0.5 to 10 µm, more preferably from 1 to 5 µm, is added to the excipient mixture. Processes for producing the inhalable powders according to the invention by grinding and micronising and finally mixing the ingredients together are known from the prior art. The inhalable powders according to the invention may be administered using inhalers known from the prior art.

The inhalation aerosols containing propellant gas according to the invention may contain the compounds 1 dissolved in the propellant gas or in dispersed form. The compounds 1 may be contained in separate formulations or in a common formulation, in which the compounds 1 are either both dissolved, both dispersed or in each case only one component is dissolved and the other is dispersed. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The abovementioned propellant gases may be used on their own or in admixture. Particularly preferred propellant gases are halogenated alkane derivatives selected from TG134a and TG227 and mixtures thereof. The propellant-driven inhalation aerosols may also contain other ingredients such as co-solvents, stabilisers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers).

Moreover, the active substances 1 according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is up to 70 percent by volume, more particularly up to 60 percent by volume and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

According to the invention, the addition of editic acid (EDTA) or one of the known salts thereof, sodium edetate, as stabiliser or complexing agent may be unnecessary in these formulations. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred.

Co-solvents and/or other excipients may be added to the propellant-free inhalable solutions according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the active substance 1, only benzalkonium chloride and sodium edetate. In another preferred embodiment, no sodium edetate is present.

The dosage of the compounds according to the invention is naturally highly dependent on the method of administration and the complaint which is being treated. When administered by inhalation the compounds of formula 1 are characterised by a high potency even at doses in the µg range. The compounds of formula 1 may also be used effectively above the µg range. The dosage may then be in the gram range, for example. Particularly when administered by routes other than by inhalation the compounds according to the invention may be administered in higher doses (for example, but not restrictively, in the range from 1 to 1000 mg).

The following examples of formulations illustrate the present invention without restricting its scope:

Examples of Pharmaceutical Formulations

| A) Tablets | |
|---|---|
| | per tablet |
| active substance 1 | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | |
|---|---|
| | per tablet |
| active substance 1 | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) Ampoule solution | |
|---|---|
| active substance 1 | 50 mg |
| sodium chloride | 50 mg |
| water for inj. | 5 ml |

The active substance is dissolved in water at its own pH or optionally at pH 5.5 to 6.5 and sodium chloride is added to make the solution isotonic. The resulting solution is filtered to remove pyrogens and the filtrate is transferred under aseptic conditions into ampoules which are then sterilised and heat-sealed. The ampoules contain 5 mg, 25 mg and 50 mg of active substance.

| D) Metering aerosol | |
|---|---|
| active substance 1 | 0.005 |
| Sorbitan trioleate | 0.1 |
| Monofluorotrichloromethane and Difluorodichloromethane 2:3 | ad 100 |

The suspension is transferred into a conventional aerosol container with metering valve. Preferably 50 µl suspension are released on each actuation. The active substance may also be released in higher doses if desired (e.g. 0.02 wt.-%).

| E) Solutions (in mg/100 ml) | |
|---|---|
| active substance 1 | 333.3 mg |
| formoterol fumarate | 333.3 mg |
| benzalkonium chloride | 10.0 mg |
| EDTA | 50.0 mg |
| HCl (1n) | ad pH 3.4 |

This solution may be prepared in the usual way.

| F) Inhalable powder | |
|---|---|
| active substance 1 | 6 µg |
| formoterol fumarate | 6 µg |
| lactose monohydrate | ad 25 mg |

The inhalable powder is prepared in the usual way by mixing the individual ingredients.

| G) Inhalable powder | |
|---|---|
| active substance 1 | 10 µg |
| lactose monohydrate | ad 5 mg |

The inhalable powder is prepared in the usual way by mixing the individual ingredients.

What is claimed is:

1. Tropan-6exo-yl benzilate methobromide or a physiologically acceptable salt thereof.
2. Tropan-6exo-yl 9-hydroxy-fluorene-9-carboxilate methobromide or a physiologically acceptable salt thereof.
3. Tropan-6exo-yl 2-hydroxy-2,2-dithiophene-acetate methobromide or a physiologically acceptable salt thereof.
4. Tropan-6exo-yl 9-hydroxy-xanthene-9-carboxilate methobromide or a physiologically acceptable salt thereof.
5. Tropan-6endo-yl benzilate methobromide or a physiologically acceptable salt thereof.
6. Tropan-6endo-yl 9-hydroxy-fluorene-9-carboxylate methobromide or a physiologically acceptable salt thereof.
7. Tropan-6endo-yl 9-hydroxy-xanthene-9-carboxilate methobromide or a physiologically acceptable salt thereof.
8. Tropan-6endo-yl 2-hydroxy-2,2-dithiophene-acetate methobromide or a physiologically acceptable salt thereof.
9. A pharmaceutical composition comprising a compound according to any one of claims 1 to 8, together with a pharmaceutical acceptable carrier, excipient or diluent.
10. A method for treating asthma, COPD, spasms in the gastrointestinal tract or spasms in the urinary tract comprising administering to a patient in need of such treatment a therapeutically effective amount of a compound according to any one of claims 1 to 8.

* * * * *